United States Patent [19]

Davie

[11] Patent Number: 5,091,058
[45] Date of Patent: Feb. 25, 1992

[54] PURIFIED PARA-CUMYLPHENOL

[75] Inventor: William R. Davie, Hopewell, Pa.

[73] Assignee: Aristech Chemical Corporation, Pittsburgh, Pa.

[21] Appl. No.: 645,775

[22] Filed: Jan. 25, 1991

Related U.S. Application Data

[63] Continuation-in-part of Ser. No. 481,926, Feb. 20, 1990, abandoned.

[51] Int. Cl.$^5$ .................. B01D 3/10; B01D 3/34; C07C 37/74
[52] U.S. Cl. .................. 203/33; 203/36; 203/37; 203/91; 203/DIG. 6; 568/744; 568/756
[58] Field of Search .................. 203/29, 33, 36, 37, 203/91, DIG. 6; 568/744, 756

[56] References Cited

U.S. PATENT DOCUMENTS

| | | | |
|---|---|---|---|
| 2,423,802 | 7/1947 | Slotterbeck et al. | 568/744 |
| 2,432,356 | 12/1947 | Underwood | 568/744 |
| 2,728,795 | 12/1955 | Armstrong et al. | 568/744 |
| 2,750,424 | 6/1956 | Armstrong et al. | 260/619 |
| 2,750,426 | 6/1956 | Armstrong et al. | 260/619 |
| 2,769,844 | 11/1956 | Joris | 260/619 |
| 4,267,379 | 5/1981 | Austin et al. | 585/435 |
| 4,351,967 | 9/1982 | Nishimura et al. | 203/64 |
| 4,906,791 | 3/1990 | Imanari et al. | 568/744 |

FOREIGN PATENT DOCUMENTS 0188535  11/1982  Japan .................. 568/744

*Primary Examiner*—Virginia Manoharan
*Attorney, Agent, or Firm*—William L. Krayer

[57] ABSTRACT

Method of preparing para-cumylphenol including reacting an excess of phenol with alpha-methylstyrene by the slow addition of alpha-methylstyrene to a 50% to 200% molar excess of phenol at a temperature from about 80° C. to about 90° C. in the presence of an acid catalyst and thereafter maintaining the temperature at about 95° to about 100° C. to obtain a crude cumylphenol reaction product containing acid derived from the catalyst, and distilling the reaction product in the presence of an amount of base sufficient to neutralize the acid therein.

5 Claims, No Drawings

PURIFIED PARA-CUMYLPHENOL

This is a continuation-in-part of my co-pending application Ser. No. 481,926, filed Feb. 20, 1990, also entitled "Purified Para-Cumylphenol", now abandoned.

TECHNICAL FIELD

This invention relates to the preparation of cumylphenol and particularly to the preparation of pure para-cumylphenol; it involves the reaction of alpha-methylstyrene and phenol to make a crude cumylphenol and then distilling the crude product under certain conditions including the presence of a base such as sodium bicarbonate.

BACKGROUND OF THE INVENTION

Para-cumylphenol is a known compound. It is known to make para-cumylphenol (PCP) by the reaction of alpha-methylstyrene (AMS) and phenol:

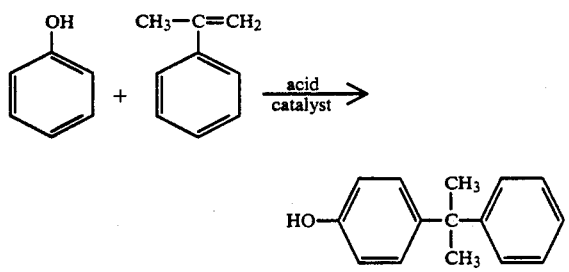

The reaction product commonly includes a number of related compounds and typically also a significant amount of unreacted phenol. Accordingly, the desired para-cumylphenol can be obtained from the crude product by distillation. However, even with careful distillation, various impurities are commonly found in the distillate. See also Armstrong et al U.S. Pat. No. 2,750,424. In Armstrong et al U.S. Pat. No. 2,750,426, the inventors recite the extraction of cumylphenol from a distillate through the use of a 5% sodium hydroxide solution.

A pure para-cumylphenol product, preferably greater than 99.5%, is desirable for use as a chain terminator in polycarbonates—see, for example, Bostian et al U.S. Pat. No. 3,466,260. But, prior to the present invention, an economically expedient method of making a pure para-cumylphenol has not been known.

SUMMARY OF THE INVENTION

My invention in one aspect is the preparation of pure para-cumylphenol from a crude cumylphenol which has been made in the presence of an acid catalyst under carefully controlled conditions and in distilling the crude cumylphenol in the presence of a base such as sodium bicarbonate. In another aspect, my invention is a method of preparing relatively pure para-cumylphenol by reacting alpha-methylstyrene with phenol in the presence of an acid catalyst, and then distilling the reaction product in the presence of a base such as sodium bicarbonate. In another aspect, my invention includes the slow addition of AMS to an excess of phenol and an acid catalyst at a temperature about 80° C. to about 110° C., separating the catalyst, adding a small amount of base (such as sodium bicarbonate) to the crude reaction mixture to neutralize any residual acidity, and employing distillation to obtain pure product.

DETAILED DESCRIPTION OF THE INVENTION

I minimize the impurities in the crude para-cumylphenol ("PCP") made by the reaction of alpha-methylstyrene ("AMS") and phenol by adding the AMS slowly to the phenol and catalyst, while maintaining the temperature at about 80° C. to about 110° C. Thereafter, the catalyst is separated from the crude reaction mixture and the impurities are further greatly reduced by distilling the crude cumylphenol in the presence of a base. The base should be sufficient to neutralize any residual acid. Any of the common inorganic bases may be used, such as alkali metal and alkaline earth metal hydroxides, carbonates and bicarbonates.

It is important that an excess of phenol be used in addition to the slow addition of AMS to the phenol and catalyst. If these conditions are not met, there will be excessive self-condensation of the AMS to dimers and excessive formation of dicumylphenol. I prefer a 50% molar excess to 200% molar excess of phenol.

Reaction temperature is also important in minimizing side reaction products such as o-cumylphenol and dicumylphenol. Formation of these two side products is favored by the higher temperatures so their concentration in the crude reaction mixture can be twice as high at 110° C. as at 90° C. reactor temperature.

On the other hand, if reactor temperature is too low, such as below 80° C., AMS dimers do not isomerize well and the product PCP must be separated with difficulty from the mixture of dimers. The preferred technique is to hold reactor temperatures low (80° to 90° C.) during the AMS addition to minimize formation of o-cumylphenol and dicumylphenol. Then after the addition of AMS has been completed over about a two-hour period, the reactor temperature is increased to about 95°–100° C. and maintained there for an hour or two to isomerize the AMS dimers.

In the study of the reaction of phenol with AMS, I have found that several side reactions occur.

In addition to PCP, the reaction can produce ortho-cumylphenol (OCP) and dicumylphenol (DCP). Although these are not difficult to separate from PCP by distillation, their presence is undesirable. During distillation, even under alkaline conditions to stabilize PCP, they dissociate slowly to produce AMS which lowers product purity. The OCP dissociates to AMS and phenol while the DCP dissociates to PCP and AMS. I have found that formation of OCP and DCP is favored by higher temperatures and longer reaction times in the presence of the acid catalyst.

Another class of side products is due to the self-condensation of AMS to produce dimers and trimers. These products can be minimized by using an excess of phenol and by slow addition of the AMS to the blend of phenol and acid catalyst. Even with this technique, however, the presence of AMS dimers cannot be eliminated.

I then studied formation and properties of the AMS dimers. I found that under mild reaction conditions such as low temperatures (under 80° C.) or partially deactivated catalyst (presence of water or methanol for example), two major dimer isomers were formed along with traces of other dimers and trimers.

The AMS dimers initially formed under mild conditions are unstable and the reaction is reversible. In fact, these dimers can be added to phenol and the acid catalyst under the conditions used to make PCP from phenol and AMS (monomer) and the yield of PCP is almost as good as if AMS monomer is used.

However, if the initially formed AMS dimers and trimers are subjected to more severe conditions (higher temperature or more active, anhydrous catalyst), they are predominantly converted to trimethylphenylindane (TMPI). This material is very stable to both acids and bases even at temperatures well above 200° C.

The presence of the unstable isomers of AMS in PCP distillation is undesirable since their boiling points are close below that of PCP and during the distillation, even under alkaline conditions they slowly dissociate to produce AMS.

Approximate boiling points at 50 mm (absolute) pressure and stability information on reaction products in PCP are tabulated below:

| Component | Boiling Point (50 mm) | Acidic Conditions | Basic Condition at Boiling Point |
|---|---|---|---|
| OCP | 204° C. | Very Unstable | Slow Dissociation |
| TMPI | 204° C. | Very Stable | Very Stable |
| AMS dimer #1 | 213° C. | Very Unstable | Slow Dissociation |
| AMS dimer #2 | 217° C. | Very Unstable | Slow Dissociation |
| Other AMS "Dimers" formed in low concentrations are likely similar to dimers #1 and #2 since they also can be converted to TMPI. | | | |
| PCP | 234° C. | Very Unstable | Stable |
| AMS trimers | Well Above 250° C. | Most are Unstable | Slow Dissociation |
| DCP | Well Above 250° C. | Very Unstable | Slow Dissociation |

As can be seen from the boiling points, OCP and TMPI are not difficult to separate from PCP but the two other major AMS dimers boil so close to PCP that distillation to achieve 99+% purity PCP is not practical.

From this information it can be seen that it is essential that maximum purity crude PCP be produced for the distillation. If possible, the AMS dimer and trimers should have been reacted with phenol to produce PCP or else have been convered to the stable, lower boiling AMS dimer, TMPI.

To favor conversion of other AMS dimers and trimers to TMPI, active catalyst, higher reaction temperature, and longer reaction times are desired. However, these conditions also favor gradual dissociation of PCP.

I have found the optimum conditions for preparation of the crude PCP to be slow addition of AMS over a period of 1 ½-2 hours to a stirred mixture of phenol and the active anhydrous acid catalyst (preferably a strongly acidic ion exchange resin such as Amberlyst 15) maintained at 80° C. The mix is stirred an additional 10 to 15 minutes after AMS addition is complete then the product is separated from resin. A slightly inactivated catalyst may require higher temperature or longer time. At this point a gas chromatographic analysis can indicate as high as 95% PCP on a phenol-free basis with the major impurities being OCP, TMPI, and DCP with only traces of other AMS dimers and AMS trimers. Longer reaction times, higher temperatures, and partially deactivated catalyst can all cause greatly lowered PCP content in the crude product. If at this point the analysis indicates more than traces of the other AMS dimers are present, some longer reaction time or slightly higher temperature is necessary.

The following narrative describes a series of experiments which demonstrate my invention:

The crude cumylphenol used in these tests was prepared by the reaction of alpha-methylstyrene (one mole) with phenol (3 moles) in the presence of Amberlyst 15 (Rohm & Haas sulfonic acid type ion exchange resin) at 80° C. The crude reaction mixture contained about 50 percent cumylphenol, the rest comprised about 50 percent of phenol and side products.

The crude composite of several batches was split into two 1.5-liter portions and both were batch distilled in an identical manner except that one was "neutralized" by addition of 1 gram of solid sodium bicarbonate to the distillation flask before the distillation was started. The fores and product were distilled through a 12-inch-long packed column under vacuum.

The "phenol cut" was distilled at 50 mm of Hg (vapor temperature about 105° C.) with the pot temperature rising from about 120° C. initially to 200° C. finally, when phenol distillation essentially ceased and the vapor temperature was rising.

The "phenol cut" is essentially pure phenol but may contain some cumene or alkylbenzenes that may have been present as trace impurities in the AMS. Generally, that cut contains little if any unreacted AMS.

An intermediate cut was removed at pot temperatures from 200° to about 240° C. and vapor temperature over the range of 105° to 230° C. at 50 mm.

The intermediate cut contains some of the phenol, the stable AMS dimer (TMPI), o-cumylphenol, and some of the PCP.

The product cumylphenol was distilled at about 234° C. vapor temperature with the pot rising from 240° to about 270° C. at 50 mm. A pot holdup of about 50 to 100 cc remained (mainly cumylphenol and heavies). The heavies were mainly AMS trimers, and dicumylphenol. Pot holdup from the non-neutralized run was not significantly greater than the neutralized run, but it was much darker in color and more viscous. After aging about 3 weeks in the oven at 80° C., the APHA colors were determined on the various sample cuts. The non-neutralized run intermediate cut had an APHA much greater than 500; the neutralized run intermediate cut APHA 30; non-neutralized run product APHA 20, 98.6 percent purity (0.3% phenol and 1.1% AMS dimer in product); neutralized run product APHA <10, 99.7% purity (0.1% phenol and 0.2% AMS dimer in product). From these results, it is evident that the neutralization improved both product color and product purity.

In deliberate attempts to cleave pure cumylphenol with an acid such as a trace of sulfuric acid, the following phenomena were observed: as would be expected, alpha-methylstyrene and phenol distilled over together at about 100° C. vapor temperature under vacuum but as the distillation continued, acidic vapor (such as sulfur dioxide) was formed and distilled over with the cleavage products. Suddenly, the receiver became hot (reaction of AMS with phenol and with itself) and when the contents of the receiver were analyzed, little AMS and phenol were present and the major portion was the reaction product (AMS dimers and cumylphenols). The same sort of results were obtained when a non-volatile acidic catalyst (Amberlyst 15) was used to catalyze the cleavage. Apparently, traces of acidity from it also distilled over with the AMS and phenol to cause their recombination in the receiver.

When the crude cumylphenol is distilled without neutralization, traces of residual acidity from the resin catalyst cause dissociation and/or recombination products to contaminate the product cumylphenol.

It should be noted that, in the presence of an acid, in addition to reacting with phenol, AMS can react with itself to produce at least four different compounds. I have found that the reaction of AMS with itself can be minimized by adding AMS very slowly to a mixture of phenol and the acid catalyst.

As stated previously, the AMS self-reaction products (mainly dimers) are undesirable in the distillation of PCP, because at least two of them distill at almost the same temperature as PCP. However, by good temperature control during the addition of AMS to the phenol reaction mixture, not only can the amount of AMS dimers be reduced, but those boiling closest to PCP can essentially be eliminated. At lower reaction temperatures, such as 60° C., the reaction of AMS with phenol proceeds quite well, but all of the AMS dimer isomers other than TMPI are produced and are stable at that temperature. Near 100° C. reaction temperature, the isomers boiling closest to PCP are not present and, in fact, if some are deliberately added to the reaction mixture, they actually react with phenol to produce PCP and the non-troublesome isomer (TMPI).

If the reaction temperature is too high, such as 120° C. or higher, however, PCP can dissociate to AMS and phenol and the AMS can then recombine to give higher yields of AMS dimers, cumylphenol and TMPI.

The catalyst I prefer for the condensation is an acidic ion exchange resin since it can be easily removed from the reaction mixture by filtration or decanting the liquid. Presumably the resin and all acidity are removed when the liquid is separated from the solid catalyst, but attempts to vacuum distill the crude product to produce pure PCP were not successful. The product contained small amounts of phenol and AMS along with recombination products other than PCP.

Apparently even the supposedly insoluble ion exchange resin left traces of acidity in the PCP and this catalyzed the dissociation (to phenol and AMS). Traces of volatile acidic material apparently distilled overhead (e.g., sulfur dioxide or sulfuric or sulfonic acids) to cause recombination in the distillation receiver.

This dissociation in the presence of acid at elevated temperature was not unexpected, since bisphenol-A (BPA) readily dissociates under those conditions. The BPA molecule is identical to the PCP molecule except that BPA has phenolic hydroxyl groups on both aromatic rings, while PCP has only one hydroxyl group. Acidic contamination in the distillation step, even in traces, should be avoided.

The very surprising finding was that the presence of base stabilizes PCP and the addition of even traces of a base, such as sodium bicarbonate, permits distillation of PCP to produce product of 9.5+ percent purity, containing essentially no phenol or AMS. In contrast, BPA is very unstable in the presence of even traces of bases and will dissociate rapidly and completely above about 180° C. PCP, on the other hand, in the presence of even large amounts of base, dissociates only very slowly even at 325° C. (In one test, it was 1-2% per hour at 325° C.)

The distillation of crude PCP preferably is carried out at 25 to 200 mm pressure so that the liquid contents of the pot are not heated above about 275° C.

Addition of as little as 1 gram of sodium bicarbonate to the distillation pot containing 2 kg of crude PCP reaction mixture was adequate to stabilize it. The use of fresh ion exchange resin seemed to impart more acidity to the crude PCP mixture so a greater quantity of base was required to stabilize this crude PCP during distillation.

The choice of base is not critical—sodium or potassium hydroxides, carbonates, and bicarbonates are all satisfactory, along with corresponding calcium or magnesium bases, but they normally have no advantage over the inexpensive, nonhygroscopic, noncorrosive sodium bicarbonate.

In summary, my process for the manufacture of PCP involves:

A. Slow addition of AMS to an excess of phenol and the acid catalyst, at about 80° C. to about 110° C., preferably below 100° C. The particular acid catalyst is not critical in this case. Any common acid, such as hydrochloric, sulfuric, and even sulfur dioxide, or cumyl chloride will catalyze the reaction of AMS with phenol.

B. Separating the crude reaction mixture from the acidic catalyst. This is very conveniently accomplished if the acidic catalyst is a solid ion exchange resin.

C. Stabilizing the crude reaction mixture for distillation by addition of sufficient base to neutralize residual acidity.

D. Distillation of the reaction mixture under vacuum (25 to 200 mm) through an appropriate column to remove excess phenol and traces of unreacted AMS. This is followed by distillation of an intermediate cut of AMS "dimers" and o-cumylphenol and finally distillation of pure PCP.

Example I describes a representative laboratory preparation.

EXAMPLE I

Condensation of Phenol with AMS

A 2-liter, 3-neck flask equipped with thermometer, dropping funnel, air condenser, and magnetic stirrer is located in a hot water bath.

To 40 grams of recycled Amberlyst 15 (strong acid sulfonic type ion exchange resin) from a liquid heel of the previous reaction batch after most of the crude reaction mixture had been siphoned off, was added about 6 moles (528 cc) of molten phenol. After the flask and stirred contents rose above 80° C., dropwise addition of the following mixed solution was started:

6 moles (528 cc) molten phenol
4 moles (520 cc) AMS

The solution was added over a period of three hours. The reaction was exothermic so the flask contents rose to about 98°-102° C. After the addition was completed, the pot contents were held at 100°-105° C. for one hour. The reaction mixture at completion contained about 50 percent phenol and 50 percent of reactants—mainly PCP. By GC analysis it contained 92.1 percent PCP on a phenol-free basis. The AMS "dimers", o-cumylphenol, dicumylphenol and AMS trimers totaled 7.9 percent (phenol-free basis) with 7.6 percent being "non-troublesome components", and only 0.3 percent of the dimer that boils closest to PCP.

After the run was completed, the stirrer was shut off and the resin rapidly settled. Most of the crude reaction product was siphoned off the resin and another batch was started with the "heel" and recovered resin.

Removal of Catalyst

The crude reaction product, after being siphoned off was filtered to remove traces of fragmented resin particles; generally, there was almost none. Several batches of crude product were composited for distillation studies.

Distillation of Crude PCP; Addition of Base

A 2-liter, 3-neck flask was equipped with heating mantle, magnetic stirrer, pot thermometer with temperature controller, 12-inch packed column, stillhead with condenser (using warm water to prevent phenol and PCP from solidifying) and thermometer, and vacuum source controlled to 25 or 50 mm pressure.

For the distillation the flask was filled (not quite full—to allow for expansion when heated) and 1 gram of sodium bicarbonate was added (none added in control test runs). Distillation was then started at 50 mm pressure.

A "phenol cut" of 99+ percent phenol was removed first (about 50% of the charge to the pot) at a vapor temperature of about 105° C. at 50 mm as the pot temperature gradually rose from 120° C. to 200° C.

An intermediate cut (phenol, AMS "dimers", o-cumylphenol, and PCP) was then removed as the vapor temperature rose from 105° C. to 230° C. and pot temperature rose from 200° C. up to 240° C. at 50 mm. This contained about 5 percent phenol, 44 percent AMS "dimers" (mainly TMPI) plus o-cumylphenol, and 50+ percent PCP. A product cut was taken starting at pot temperature 240° C. and vapor temperature 230°–235° C. at 50 mm.

Analysis of product cut from sodium bicarbonate neutralized run:
Phenol 0.1%   AMS dimer 0.2%   PCP 99.7%
APHA color after two weeks aging at 80° C. was <10.

Analysis of product cut from non-neutralized run:
Phenol 0.3%   AMS dimer 1.1%   PCP 98.6%
APHA color after two weeks aging at 80° C. was 20.

EXAMPLE 2 (COMPARATIVE)

When a distillation of product prepared using previously unused Amberlyst 15 and not neutralized with bicarbonate lower purity PCP, 98.0 percent, and higher color, APHA 70, resulted. This result indicates fresh Amberlyst 15 contains more free acid.

I claim:

1. Method of preparing para-cumylphenol comprising reacting an excess of phenol with alpha-methylstyrene by the slow addition of alpha-methylstyrene to a 50% to 200% molar excess of phenol at a temperature from about 80° C. to about 90° C. in the presence of an acid catalyst and thereafter maintaining the temperature at about 95° to about 100° C. to obtain a crude cumylphenol reaction produce containing acid derived from said catalyst, and stilling the reaction product in the presence of an amount of base sufficient to neutralize the acid therein.

2. Method of claim 1 wherein the base is sodium bicarbonate.

3. Method of claim 1 wherein the distillation is conducted under vacuum.

4. Method of claim 1 wherein the acid catalyst is an acid ion exchange resin.

5. Method of claim 1 wherein the distillation of the reaction product is conducted at about 25 to about 200 mm pressure.

* * * * *

UNITED STATES PATENT AND TRADEMARK OFFICE
CERTIFICATE OF CORRECTION

PATENT NO.   : 5,091,058
DATED        : 2/25/92
INVENTOR(S)  : William R. Davie

It is certified that error appears in the above-identified patent and that said Letters Patent is hereby corrected as shown below:

Column 5, line 59, change "9.5+" to -- 99.5+ --.

Column 8, line 25, claim 1, change "produce" to -- product --;
          line 26, claim 1, change "stilling" to -- distilling --.

Signed and Sealed this

Fourteenth Day of September, 1993

Attest:

BRUCE LEHMAN

Attesting Officer

Commissioner of Patents and Trademarks